US006008053A

United States Patent [19]
Williams

[11] Patent Number: 6,008,053
[45] Date of Patent: Dec. 28, 1999

[54] MEASUREMENT OF FEED DIGESTIBILITY IN RUMINANTS

[75] Inventor: Peter Williams, Plaisir, France

[73] Assignee: Rhone-Poulenc Nutrition Animale, Antony, France

[21] Appl. No.: 09/011,605

[22] PCT Filed: Aug. 7, 1996

[86] PCT No.: PCT/FR96/01255

§ 371 Date: Feb. 10, 1998

§ 102(e) Date: Feb. 10, 1998

[87] PCT Pub. No.: WO97/06434

PCT Pub. Date: Feb. 20, 1997

[30] Foreign Application Priority Data

Aug. 10, 1995 [FR] France ................................. 95 09710

[51] Int. Cl.$^6$ .......................... G01N 31/00; G01N 33/02; G01N 21/29; A01K 29/00; A01K 43/00
[52] U.S. Cl. ............................... 436/20; 436/17.1; 426/2; 426/231; 422/82.05
[58] Field of Search .................... 426/2, 231; 436/20, 436/17.1; 422/82.05

[56] References Cited

U.S. PATENT DOCUMENTS

| | | | |
|---|---|---|---|
| 5,173,430 | 12/1992 | Edwards et al. ........................... | 436/20 |
| 5,728,920 | 3/1998 | Leudtke et al. .......................... | 800/200 |
| 5,747,020 | 5/1998 | Rutherford et al. ................. | 424/93.45 |

FOREIGN PATENT DOCUMENTS 254594  3/1988  Germany.

OTHER PUBLICATIONS

Sanderson et al. "Use of Near Infrared Reflectance Spectroscopy to Predict and Compare the Composition of Corcaso Sapler From Young Steers" Animal Science 65 (1), 45–54, 1997.

Sinnaeve et al "The Use of Near Infrared–Spectroscopy for the Analysis of Fresh Grass–Silage". J. Near Infrared Spectrose. 2(2) 79–84 Abstract only, 1994.

Hsu et al. Use of Near Infrared Spectroscopy for Determining Protein Fractions in Alfalfa. Near Infrared Spectrosc. Future Wavas, Proc. Int. Conf. Near Infrared Spechosc. 7$^{th}$ (1996) 581–587, 1996.

Park et al. The Use of Near Infrared Reflectace Spectroscopy on Dried Saple to Predict Biological Parameters of Grass Silage. Animal Feed Sci. Techol. 68(3–4) 235–246, 1997.

Amari et al Estimation of Chemical Composition and Nutritive Value of Forages Nnear Infrared Reflectance Spectroscopy. Nippon Sochi Gakkeishi 34 (4) 271–9, 1989.

Amari et al Prediction of Chemical Composition and Nutritive Value of Forages by Near Infrared Reflectance Spectroscopy. I. Prediction of Chemical Composition Nippon Sochi Gakkaishi 33(3) 219–26, 1987.

De La Roza et al The Use of Near Infrared Reflectance Spectroscopy to Predict the Nutritive Value and in Vivo Digestibility of Grass Silages Making Light Work: Adv. Near Infrared Spectrosc. Int. Conf. Near Infrared Spectrosc, Meeting Date 1991, 269–71. Editors Murray et al; Publisher VCH, Weinheim Germany, 1992.

Antoniewicz et al., "Rumen Degradability of Crude Protein of Dried Grass and Lucerne Forage Measured by in Sacco Incubation and Predicted by Near Infrared Spectroscopy, "Animal Feed Science and Technology, 54:203–216 (1995).

Dardenne et al., "Composition and Nutritive Value of Whole Maize Plants Fed Fresh to Sheep. II. Prediction of the in vivo Organic Matter Digestibility," Annals of Zootech 42:(3):251–270 (1993).

Downey et al., "Dried Grass Silage Analysis by Nir Reflectance Spectroscopy—a Comparison of Stepwise Multiple Linear and Principal Component Techniques for Calibration Development on Raw and Transformed Spectral Data," Journal of Chemometrics, 3(2):397–407 (1989).

*Primary Examiner*—Randy Gulakowski
*Assistant Examiner*—Paul J. Lee
*Attorney, Agent, or Firm*—Finnegan, Henderson, Farabow, Garrett & Dunner, L.L.P.

[57] ABSTRACT

A method for determining in vivo the nutritional value of animal feed during the transit of the feed in the digestive system of ruminant comprising analysing said feed, more particularly ensilage, by near infrared spectrophotometry.

6 Claims, 1 Drawing Sheet

MEASUREMENT OF FEED DIGESTIBILITY IN RUMINANTS

CROSS-REFERENCE TO RELATED APPLICATIONS

This application is a national stage application under 35 U.S.C. §371, filed Feb. 10, 1998, of international application PCT/FR96/01255 filed Aug. 7, 1996.

The present invention relates to a novel process for determining the nutritional value of silage given to ruminants. It has long been sought to optimize the nutritional value of feeds given to reared animals in order to increase, in particular in ruminants, milk and/or meat production.

DESCRIPTION OF THE RELATED ART

It is known, for example according to the publications published in Can. J. Anim. Sci. 67;557–562 (Jun. 1987) that it is possible to determine both the "in vitro" digestibility of various corn hybrids and the same digestibility by a method of determination by near-infra-red spectrophotometry.

It is also known, according to the article from the following authors: Valdes, Hunter and Pinter, published in Can. J. Plant Sci. 67;747–754 (Jul. 1987) to determine the IVMD (in vitro dry-matter digestibility) values which were hitherto obtained by an "in vitro" ruminal fermentation technique described by Tilley and Terry in 1963, by a method of near-infra-red spectrophotometric analysis.

The methods described in the above two publications have made it possible to combine "in vitro" digestibility analysis methods with near-infra-red spectrophotometric analysis methods. This combination for estimating the "in vivo" digestibility of chemical and enzymatic analysis methods, which themselves have large variabilities, with a near-infra-red spectrophotometric method which itself also has a large variability made it possible to obtain fairly moderate evaluations of the digestibility.

As regards the prediction of the "in vivo" digestibility by near-infra-red spectrophotometric analysis, no publication has appeared to date. Other publications combining "in vitro" analyses with near-infra-red spectrophotometry have been published, such as the publication by Dardenne, Andrieu, Barrière, Biston, Demarquilly, Femenias, Lila, Maupetit, Rivière and Ronsin, Ann. Zootech (1993) 42, 251–270 which established calibration curves for the following analyses: dry matter, ash, total proteins, water-soluble carbohydrates, celluloses, cell wall constituents, total fibre, acidic and neutral detergent fibre, lignin, enzymatic solubilities, determined by the methods of Aufrère, Limagrain and Lila. These various "in vitro" analyses make it possible to determine, as above, an "in vivo" digestibility value. These "in vitro" analyses have all been made possible by means of a determination by near-infra-red spectrophotometry, which has made it possible by calculation to determine an "in vivo" digestibility value.

None of these methods has hitherto combined an "in vivo" determination of the nutrient value of a silage directly with an analysis by near-infra-red spectrophotometry. This determination was not obvious on reading any of this essentially chemical and mathematical prior art, since many physiological phenomena occur in an animal's body which have never been taken into account in the chemical or enzymatic analyses performed to date and which have thus not been able to lead to a determination by near-infra-red spectrophotometry.

BRIEF SUMMARY OF THE INVENTION

The object of the present invention is the determination of the "in vivo" nutrient value of feed in ruminants by near-infra-red spectrophotometry. The invention relates more particularly to the determination of the ruminal degradability value of fodder in ruminants. The invention may also relate to the intestinal digestibility value of amino acids. Thus, this method can make it possible to determine the actual degradability value of feed during its transit through the digestive system.

DETAILED DESCRIPTION OF THE INVENTION

Figure 1:
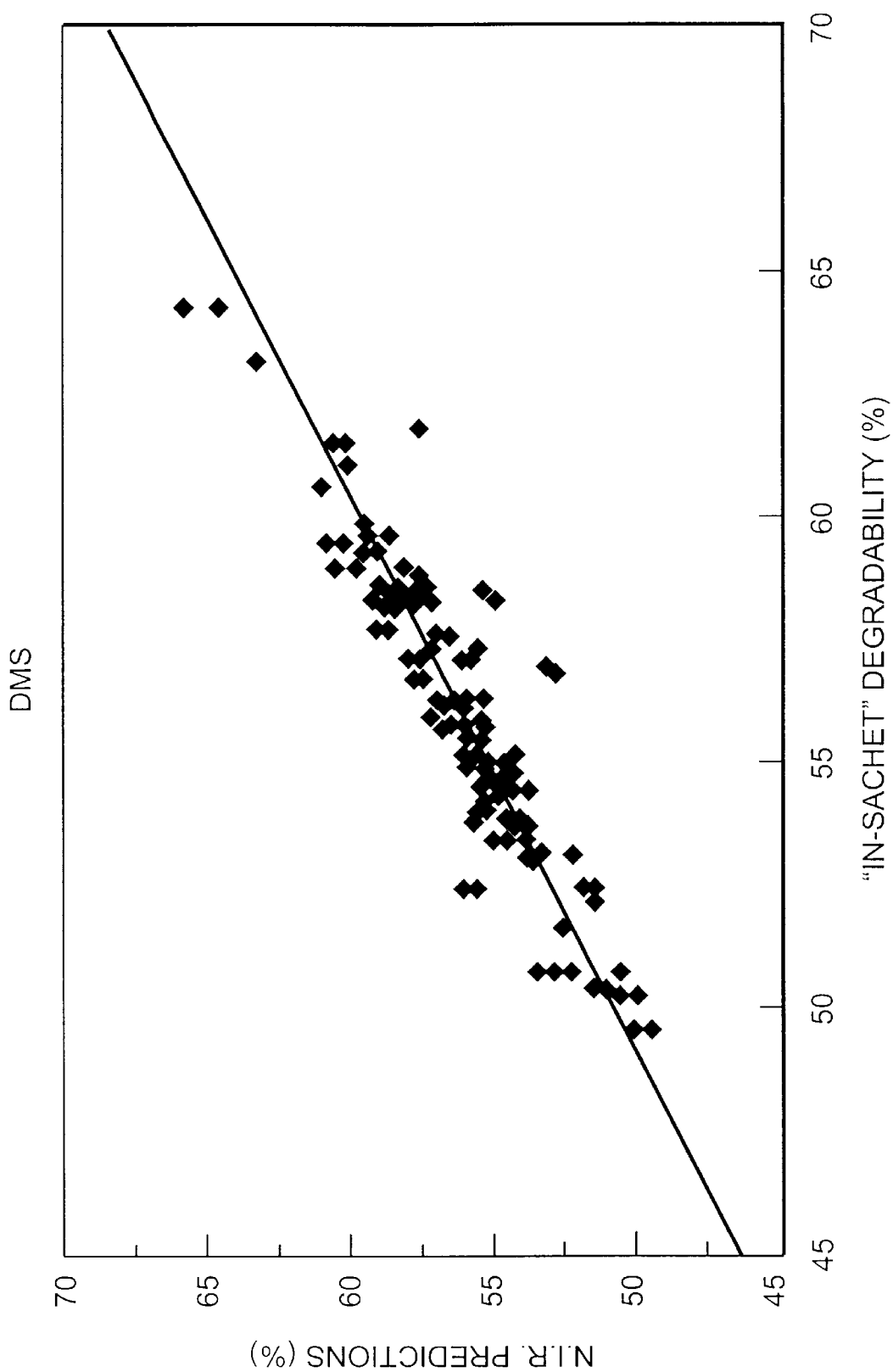
FIG. 1 is a calibration curve for DMS titled "In-sachet" degradability (%) vs. N.I.R. predictions (%).

Among the feeds whose nutritional value and ruminal degradability value can be determined by near-infra-red analysis, mention may be made of silage and most particularly of grass silage, corn silage, alfalfa silage, spent grain silage and beetroot pulp silage. These silages are preferably stored in minisilos containing about 4 kg of silage, sampling from these minisilos being more representative since it is more uniform than in standard silos.

According to a practical plan, the method for determining the ruminal digestibility consists in placing the starting material whose digestibility it is desired to determine in Nylon sachets, in placing these Nylon sachets in the rumen of cows cannulated in the rumen and in leaving the sachets in the rumen for a variable period of time, the cows being fed normally. After the chosen interval the sachets are removed, washed with water and their contents analysed.

The following chemical analyses are carried out on the silage before introduction into the rumen:

inorganic matter total nitrogenous matter starch crude cellulose

NDF (neutral detergent fibre)

ADF (acidic detergent fibre)

lignin

After the incubation period in the rumen the following analyses are performed:

total nitrogenous matter (TNM)

starch dry matter (DM)

NDF (neutral detergent fibre)

The ruminal degradabilities of nitrogen, starch, dry matter (DM) and neutral detergent fibre are determined by difference.

As regards the intestinal digestibility of the foodstuffs and more particularly of the amino acids, the process is performed as follows. The amino acid content of the sachets removed from the rumen is analysed. The sachets are introduced into a solution of pepsin and acid at pH 2 for a period of 2.5 hours. The sachets are then introduced into a cow via a duodenal cannula during the evening meal, and the sachets are collected in the droppings the following day, washed with water and then dried. At each step, the residual amount of amino acid is measured and the amount of amino acid available to the animal is determined by difference.

After obtaining the chemical and "in sachet" results, each silage sample in its ground and dried form is recorded using a spectrophotometer working in the near-infra-red region (i.e. between 700 and 2500 nm). The measurement taken is in the form of a spectrum which is in fact physicochemical data on the sample.

The following step consists in combining the N.I.R. data (spectral data) with the results determined by the standard nutrient value analyses described above. This process results in predictive equations which make it possible to determine directly, based on the N.I.R. spectrum, the nutritional value of a silage. These operations are controlled by a commercial data system, sold under the name "NIRS 2, version 3.00" and distributed by Infrasolt International I.S.I.

These operations make it possible, by a simple and inexpensive method which does not destroy the starting material, to determine the nutritional value of various types of fodder very quickly and without using mathematical calculations. This method can be used simply by any livestock farmer wishing to make modifications to improve the feed ration he gives to his animals.

The examples which follow allow the invention to be described more fully, but should not be considered as limiting it.

EXAMPLES

I-Animals

I-1. Animals 6 dry, non-gestating dairy cows of similar weight, cannulated in the rumen and the duodenum. The experiment can also be carried out on 3 cows, each sample being passed twice on the 3 cows.

I-b 2.Rationing

The ration is composed of fodder and concentrate: 7 kg of hay, 2 kg of concentrate. The animals are provided with a licking block to supply them with minerals and trace elements.

The amount of hay given is modified depending on the animal's condition.

TABLE 1

Composition of the concentrate

| STARTING MATERIAL | % |
|---|---|
| Barley | 41 |
| Dehydrated beetroot pulp | 37 |
| Soya cake 48 | 15 |
| Urea | 2 |
| Molasses | 5 |

Values in kg: 0.9 UFL—125 PDIN—100 PDIE—3 g of P—13 g of Ca.

The concentrate and fodder are given at 8.00 h and 17.00 h each day.

The animals will become adapted to the diet 3 weeks after the start of the experiment.

II—Receipt and treatment of the samples

II—1. Receipt of the samples

Opening of the minisilos, recording of the weight and the pH

The corn silage is stored in the minisilos (about 4 kg of corn silage per minisilo). These minisilos are opened about 2 months after they have been made. The contents of each minisilo are emptied into a large basin and the basin is then weighed and the amount of silage in each minisilo is recorded. The pH of the silage is measured using a pH meter at various points in this basin (at least 5 measurements per basin) and the average of the various measurements is then determined.

II—2. Treatment of the samples

Determination of the dry matter and drying of the sample

Fifty grams of silage are taken from the basin placed in an oven at 104° C. for 16 h in order to determine the dry matter. The weight of the sample is recorded at 16 h and then 2 h later. These measurements make it possible to obtain 2 values of dry matter, and the average of these two values is determined.

The remainder of the silage contained in the basin is placed in another oven at 60° C. for about 3 days. This period varies depending on the amount of silage to be dried. The basin is removed from the oven when the silage is totally dry.

Grinding of the sample

The whole sample is ground using an impact disc mill with a 3 mm screen.

The ground silage is separated into 3 samples: one sample (200 g) is sent for chemical analysis, another sample (150 g) is used for the degradation kinetics and the remaining sample is placed in a box and stored in a cold chamber at 4° C.

III—"In-sachet" methods

The Nylon sachets technique is performed using the INRA method (Michalet—Doreau 1987).

III—1. Preparation of the sachets

Characteristics of the sachets

Internal dimensions: 6–11 cm

Porosity: 48 $\mu$m

Amount of sample: 4 g

Weight/surface ratio: 30 mg/cm$^2$

Identification of the sachets: sample No., cow (A, B, C, D, E, F), kinetic No. (from 1 to 6)

Procedure

The empty sachets are left in an oven for 24 h at 80° C. They are then weighed and subsequently filled with 4 g of sample and welded. They are weighed full and attached to a ballasted chain: 36 sachets per chain.

III—2. Ruminal incubation

Each sample of silage is incubated in the 6 cows. The incubation residues are then combined by kinetic point for the analysis.

TABLE 2

Chronology of each kinetic

| 1st day | 2nd day | 3rd day |
|---|---|---|
| 7.45 h: Introduction of the 2, 4, 8, 24 and 48 h sachets | 7.45 h: Removal of the 16 h and 24 h sachets | 7.45 h: Removal of the 48 h sachets |
| 8.00 h: Meal | 8.00 h: Meal | 8.00 h: Meal |
| 9.45 h: Removal of the 2 h sachets | | |
| 11.45 h: Removal of the 4 h sachets | | |
| 15.45 h: Removal of the 8 h sachets, introduction of the 16 h sachets | | |
| 17.00 h: Meal | 17.00 h: Meal | 17.00 h: Meal |

III—3. Washing of the sachets

After removing the sachets from the rumen, they are washed with cold water in a Calor-type washing machine on a 5-min cycle until clear rinsing water is obtained. The sachets are then placed in a freezer until the end of the ruminal incubation, and then in an oven at 104° C. for 16 h. They are weighed after 16 h and then 2 h later. The lower of the 2 values is retained for the subsequent calculations.

The kinetic residues are then combined by kinetic point and sent for analysis.

IV—Analyses

IV—1. Chemical analysis on the crude product

Two hundred grams of dried and ground corn silage are sent for analysis for assay of the IM, TNM, starch, CC, NDF, ADF and lignin. The UFL and UFV values are calculated.

IV—2. Chemical analysis on the kinetic residues

Three assays are carried out on the incubation residues, and are presented in Table 3.

TABLE 3

Assays carried out on the residues

| Kinetic points | Assays |
| --- | --- |
| 2 h | TNM, starch |
| 4 h | TNM, starch |
| 8 h | TNM, starch |
| 16 h | TNM, CC |
| 24 h | TNM, CC |
| 48 h | TNM |

IV—3. Calculation of the PDI values

The PDIA, PDIE and PDIN values are calculated after the degradability kinetics and chemical analyses, taking into account the CC and TNM contents and the actual DT.

V—Near-infra-red (N.I.R.) analysis

*Treatment of the Samples

The infra-red analysis is carried out on samples which have been prepared according to the procedure described in section II—2, i.e. after drying and grinding. The amount of starting material used for this type of measurement is about 150 to 200 grams depending on the density of the product.

*Recording of the N.I.R. spectra

This operation is carried out using an N.I.R.S. 6500 type grating spectrophotometer (distributed by Perstorp Analytical Int.) operating in "reflectance" mode. One of the main specificities of this instrument is that it works over the entire near-infra-red range and not over a few specific wavelengths, as is the case for certain more standard machines.

The sample is packaged in a rectangular transportation cell composed of three opaque faces and a face fitted with quartz. After positioning the cell in the spectrophotometer, the light reflected by the sample, which carries information regarding the chemical composition of this sample, is recorded in the form of a spectrum. Each type of starting material and, consequently, each sample has a different spectrum.

*Construction of a Calibration Population

This operation consists in developing a database representative of the silages studied, using the set of samples whose spectral identity is available to hand and the "in-sachet" chemical results (TNM, NDF, ADF, DMS, DT). Statistical and spectral data are thus placed together in the same calibration file.

*Centering of the Calibration Population

The entire calibration file constructed is subjected to a statistical calculation which makes it possible to detect the presence of spectra out of the ordinary which have excessively large Mahalabonis distances (statistical distance H) relative to the average spectrum of the population (center of gravity). Once detected, these samples are removed in order to obtain a uniform population.

*Calibration

The calibration file containing the set of samples is subjected to a statistical treatment, of which various types exist: "modified partial least square" (M.P.L.S.), partial least square (P.L.S.) which is a general form of regression by main components, or alternatively "step up" which corresponds to a simpler linear regression. After the appropriate regression method has been chosen, it is preferable to carry out a mathematical treatment by derivation for all of the analyses. This mathematical treatment is determined by an evaluation sequence a, b, c, d: a=order of the derivative, b=interval in nm over which the calculation of the derivative extends, c=smoothing constant 1, d=smoothing constant 2. After initialization by the above choices, a calibration phase is launched.

A calibration curve is as depicted in FIG. 1.

*Use of the Calibration Equations

The determinations by infra-red readings on unknown silage samples are carried out using the predictive equations giving the best performance. This selection operates on the basis of various statistical parameters such as the coefficient of correlation ($R^2$) or the standard error of prediction.

I claim:

1. A process for determining an "in vivo" nutrient value of silage, said process comprising:

performing near-infra-red spectral analysis on at least one sample of undigested silage;

placing said at least one sample into at least one sachet;

introducing said at least one sachet into a rumen of a ruminant and allowing said at least one sachet to remain in the rumen for a time sufficient for digestion of said silage;

removing said at least one sachet from the rumen;

washing said at least one sachet;

chemically and enzymatically analyzing contents of said at least one removed sachet:

comparing analytical values obtained from said chemical and enzymatic analysis with the near-infra-red spectrum plotted for said undigested sample:

plotting correlation curves; and using said plotted correlation curves to estimate the nutrient value of new samples.

2. The process according to claim 1, wherein said silage is grass silage, corn silage, alfalfa silage, spent grain silage or beetroot pulp silage.

3. A process for determining ruminal degradability value of silage in a ruminant, said process comprising:

performing near-infra-red spectral analysis on at least one sample of undigested silage;

placing said at least one sample into at least one sachet;

introducing said at least one sachet into a rumen of a ruminant, allowing said at least one sachet to remain in the rumen for a time sufficient for digestion of said silage;

removing said at least one sachet from said ruminant;

performing chemical and enzymatic analysis on contents of said at least one removed sachet;

comparing analytical values resulting from the near-infrared spectral analysis of said at least one undigested sample with analytic values resulting from said chemical or enzymatic analytical analysis; and plotting a correlation curve to determine the ruminal degradability value.

4. The process according to claim 3, wherein said silage is grass silage, corn silage, alfalfa silage, spent grain silage or beetroot pulp silage.

5. A process for determining an intestinal digestibility value of amino acids in silage in a ruminant, said process comprising:

placing at least one sample of undigested silage sample into at least one sachet;

introducing said at least one sachet into a rumen of a ruminant, allowing said at least one sachet to remain in the rumen for a time sufficient for digestion of said silage;

removing said at least one sachet from said ruminant;

analyzing an amino acid content of the silage in said at least one sachet removed from the rumen;

placing said at least one analyzed sachet into a solution of pepsin and acid at pH of 2 for a period of 2.5 hours;

removing said at least one sachet from said solution;

introducing said at least one sachet into a duodenum of a ruminant via a duodenal cannula;

collecting said at least one sachet in fecal droppings;

washing and drying said at least one sachet collected from said droppings;

measuring a residual amount of amino acid in said at least one collected sachet;

comparing analytical values of the amino acid content of said at least one sachet after removal from the rumen with analytical values of the amino acid residual amounts obtained following collection of the said at least one sachet from feces of said ruminant;

and plotting a correlation curve to determine the intestinal digestibility value of said amino acids.

6. The process according to claim 5, wherein said silage is grass silage, corn silage, alfalfa silage, spent grain silage or beetroot pulp silage.

* * * * *

UNITED STATES PATENT AND TRADEMARK OFFICE
CERTIFICATE OF CORRECTION

PATENT NO.    : 6,008,053
DATED         : December 28, 1999
INVENTOR(S)   : Peter Williams It is certified that error appears in the above-identified patent and that said Letters Patent is hereby corrected as shown below:

<u>Title page,</u>
Item [54], the title, "MEASUREMENT OF FEED DIGESTIBILITY IN RUMINANTS" should read -- FEED DIGESTIBILITY MEASUREMENT IN RUMINANTS --.

Signed and Sealed this

Thirtieth Day of July, 2002

*Attest:*

JAMES E. ROGAN
*Attesting Officer*    *Director of the United States Patent and Trademark Office*